United States Patent
Wang et al.

(10) Patent No.: US 11,555,016 B2
(45) Date of Patent: Jan. 17, 2023

(54) PLEUROMULIN 7-CHLORO-1-CYCLOPROPYL-6-FLUORO-1,4-DIHYDRO-4-OXOQUINOLINE-3-CARBOXYLIC ACID ESTER WITH ANTIBACTERIAL ACTIVITY AND A METHOD OF PREPARING THE SAME

(71) Applicants: Yongbo Wang, Xi'an (CN); Han Li, Xi'an (CN); Gennian Mao, Xi'an (CN); Bin Tian, Xi'an (CN); Dan Yang, Xi'an (CN); Chengyuan Liang, Xi'an (CN); Xiuding Yang, Xi'an (CN); Wenbo Yao, Xi'an (CN); Guaiping Qiao, Xi'an (CN); Nan Hui, Xi'an (CN); Juan Li, Xi'an (CN); Liang Xin, Xi'an (CN); Jingyi Li, Xi'an (CN); Ruina Bian, Xi'an (CN)

(72) Inventors: Yongbo Wang, Xi'an (CN); Han Li, Xi'an (CN); Gennian Mao, Xi'an (CN); Bin Tian, Xi'an (CN); Dan Yang, Xi'an (CN); Chengyuan Liang, Xi'an (CN); Xiuding Yang, Xi'an (CN); Wenbo Yao, Xi'an (CN); Guaiping Qiao, Xi'an (CN); Nan Hui, Xi'an (CN); Juan Li, Xi'an (CN); Liang Xin, Xi'an (CN); Jingyi Li, Xi'an (CN); Ruina Bian, Xi'an (CN)

(73) Assignee: SHAANXI UNIVERSITY OF SCIENCE AND TECHNOLOGY, Shaanxi (CN)

(*) Notice: Subject to any disclaimer, the term of this patent is extended or adjusted under 35 U.S.C. 154(b) by 131 days.

(21) Appl. No.: 17/157,916

(22) Filed: Jan. 25, 2021

(65) Prior Publication Data
US 2022/0235008 A1 Jul. 28, 2022

(51) Int. Cl.
*C07D 215/233* (2006.01)
*A61P 31/04* (2006.01)

(52) U.S. Cl.
CPC .......... *C07D 215/233* (2013.01); *A61P 31/04* (2018.01)

(58) Field of Classification Search
CPC ...... C07D 215/233; A61P 31/04; Y02A 50/30
See application file for complete search history.

(56) References Cited

PUBLICATIONS

Farney et al., JACS, 2018, 140, 1267-1270.*

* cited by examiner

*Primary Examiner* — Sun Jae Yoo

(57) ABSTRACT

A compound with anti-drug resistant bacteria activity having the following formula (I):

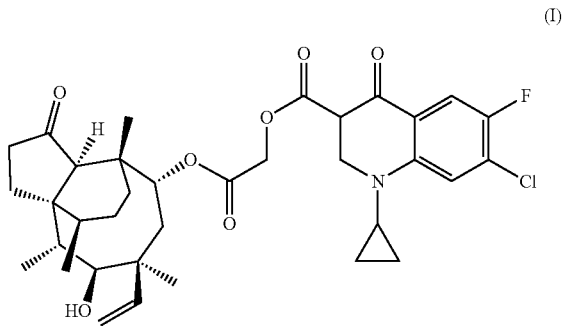

is disclosed. The methods of preparing the compound of formula (I) are also disclosed.

16 Claims, 4 Drawing Sheets

PLEUROMULIN 7-CHLORO-1-CYCLOPROPYL-6-FLUORO-1,4-DIHYDRO-4-OXOQUINOLINE-3-CARBOXYLIC ACID ESTER WITH ANTIBACTERIAL ACTIVITY AND A METHOD OF PREPARING THE SAME

FIELD OF THE INVENTION

The present invention relates to the field of medicinal chemistry, and in particular, to pleuromulin 7-chloro-1-cyclopropyl-6-fluoro-1,4-dihydro-4-oxoquinoline-3-carboxylic acid ester with antibacterial activity and a method of preparing the same.

BACKGROUND OF THE INVENTION

Antimicrobials are the most commonly used drugs for the treatment of bacterial infections. Over the years, with the popularity and application of antibiotics around the world, as well as serious unreasonable abuse, a variety of drug-resistant strains have appeared in both Gram-positive and Gram-negative bacteria. Among them, the problem of drug resistance of Gram-positive bacteria is particularly serious. Methicillin-resistant *Staphylococcus aureus* and *Staphylococcus epidermidis*, penicillin-resistant *Streptococcus pneumoniae* and vancomycin-resistant enterococci are serious clinical problems. At present, there is a lack of effective drugs for the infection caused by these drug-resistant bacteria. There is an urgent need to develop new structural antimicrobials without cross-resistance and more effective.

Pleuromulin (compound of formula (II)) belongs to tricyclic diterpenoid antibiotics. The main structure for its antibacterial effect is the tricyclic skeleton in the compound, which can form an inducing fit effect with the peptide acyltransferase active center (PTC) of the 50S subunit of the bacterial ribosome. Pleuromutilin antibiotics have certain antibacterial activity against most Gram-positive bacteria except *Enterococcus faecalis*. In addition, pleuromutilin antibiotics also have good in vitro antibacterial effects against fastidious gram-negative bacteria including *Haemophilus influenzae*, *Moraxella catarrhalis* and *Neisseria* spp. It has been more than half a century that pleuromutilin antibiotics have been discovered. Although the application of these drugs in veterinary clinics has achieved considerable results, there is no pleuromutilin antibiotics available for systemic medicine in the human medicine clinic.

7-Chloro-1-cyclopropyl-6-fluoro-1,4-dihydro-4-oxoquinoline-3-carboxylic acid (CAS: 86393-33-1) (compound of formula (IV)) is an organic intermediate. It can be used to synthesize Ciprofloxacin.

In the present invention, pleuromulin is combined with 7-chloro-1-cyclopropyl-6-fluoro-1,4-dihydro-4-oxoquinoline-3-carboxylic acid to obtain a pleuromulin 7-chloro-1-cyclopropyl-6-fluoro-1,4-dihydro-4-oxoquinoline-3-carboxylic acid ester. Preliminary in vitro antibacterial activity experiment shows that the compound has excellent antibacterial activity and anti-drug-resistant bacteria activity.

SUMMARY OF THE INVENTION

In one embodiment, the present invention provides a compound having the following formula (I):

(I)

In another embodiment, the present invention provides a method of preparing the compound of formula (I). The method includes reacting a compound of formula (II) with a compound of formula (III) to obtain the compound of formula (I).

In another embodiment, the compound of formula (III) is prepared by the following steps: adding 7-chloro-1-cyclopropyl-6-fluoro-1,4-dihydro-4-oxoquinoline-3-carboxylic acid to dichloromethane as a reaction solvent in a reactor; adding oxalyl chloride and N,N-dimethylformamide as a catalyst to the reactor under nitrogen atmosphere; stirring at 20° C. for 3 hours; and removing the reaction solvent to obtain the compound of formula (III).

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding an organic solvent and a catalytic amount of triethylamine under nitrogen atmosphere to obtain a reaction mixture; and heating the reaction mixture at 20-60° C. for 3-6 hours; and extracting the reaction mixture with ethyl acetate to obtain a crude product; and purifying the crude product on a silica gel fresh chromatography column with dichloromethane and ethyl acetate as an eluent to obtain the compound of formula (I).

In another embodiment, the organic solvent is toluene, dichloromethane or N,N-dimethylformamide.

In another embodiment, the organic solvent is dichloromethane.

In another embodiment, the molar ratio of the compound of formula (II) and the compound of formula (III) is 1:1.1.

In another embodiment, the reaction mixture is heated at 25° C.

In another embodiment, the reaction mixture is heated for 5 hours.

In another embodiment, the eluent is petroleum ether: ethyl acetate=3:2.

In another embodiment, the present invention provides a method of preparing the compound of formula (I) of claim 1, comprising: reacting the compound of formula (II) with the compound of formula (IV) to obtain the compound of formula (I).

In another embodiment, the reaction of the compound of formula (II) with the compound of formula (IV) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (IV) to the reactor to form a reaction mixture; heating the reaction mixture at 20-50° C. for 4-8 hours; placing the reaction mixture in a separating funnel to separate a crude product; purifying the crude product by recrystallization in methanol to obtain the compound of formula (I); and recycling the ionic liquid.

In another embodiment, the ionic liquid is 1-octyl-3-methylimidazo-lium hexafluorophosphate, 1-hexyl-3-methylimidazolium tetrafluoroborate, or 1-butyl-3-methylimidazolium tetrafluoroborate ([BMIM][$BF_4$]).

In another embodiment, the ionic liquid is the ionic liquid is 1-butyl-3-methylimidazolium tetrafluoroborate ([BMIM][$BF_4$]).

In another embodiment, the compound of formula (II) and the compound (IV) have a molar ratio of 1:1 to 1:1.3.

In another embodiment, the molar ratio of the compound of formula (II) and the compound of formula (IV) is 1:1.1.

In another embodiment, the reaction mixture is heated at 30° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

EXAMPLE 1

Preparation of Compound 2-(((3aS,4R,5S,6S,8R,9R,
9aR,12R)-5-hydroxy-4,6,9,12-tetramethyl-1-oxo-6-
vinyldecahydro-3a, 9-propanocyclopenta[8]annulen-
8-yl)oxy)-2-oxoethyl-7-chloro-1-cyclopropyl-6-
fluoro-4-oxo-1,2,3,4-tetrahydroquinoline-3-
carboxylate (Compound of Formula (I))

2.82 g (10 mmol) of 7-chloro-1-cyclopropyl-6-fluoro-1, 4-dihydro-4-oxoquino-line-3-carboxylic acid was dissolved in 50 mL of dichloromethane in a 250 mL three-necked flask. 1.65 g (13 mmol) of oxalyl chloride was added slowly under nitrogen atmosphere. 100 µL of N,N-dimethylformamide was added as a catalyst to the reaction mixture. The reaction mixture was stirred at 20° C. for 3 hours. After reaction was completed, dichloromethane was removed under reduced pressure to obtain 3.0 g of 7-chloro-1-cyclopropyl-6-fluoro-1,4-dihydro-4-oxoquino-line-3-carboxylic acid chloride (compound of formula (III)). The acid chloride was then used in Examples 1-12.

In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 213.7 mg (0.71 mmol) of 7-chloro-1-cyclopropyl-6-fluoro-1,4-dihydro-4-oxo-quinoline-3-carboxylic acid chloride was dissolved in 20 mL of dichloromethane, and added dropwise to the reaction mixture by a separatory funnel. After the completion of the dropwise addition, the reaction was carried out at 25° C. for 5 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 295.0 mg of the title compound, a yield of 70.56%.

Figure 4:
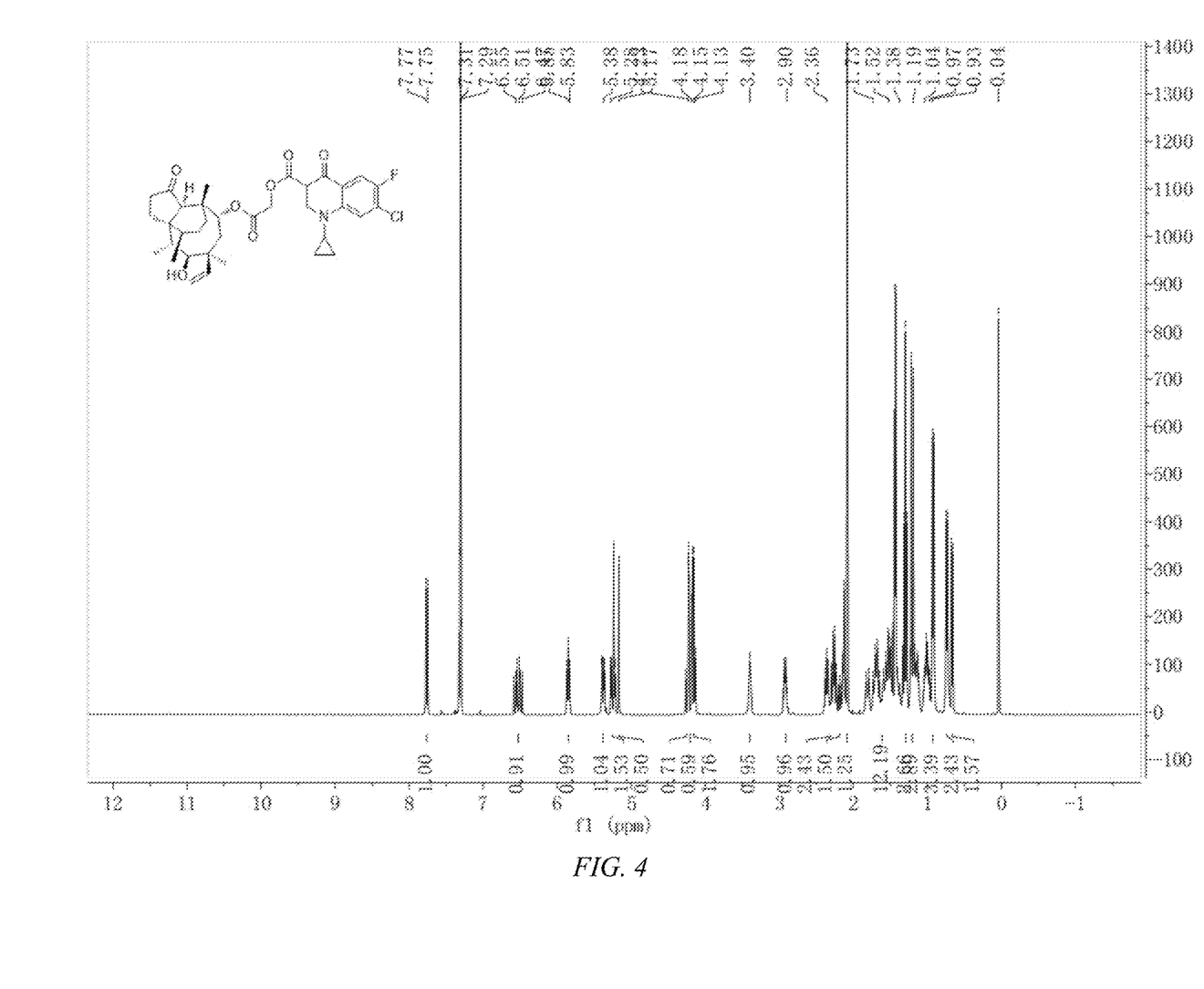
FIG. 4 is the $^1$H-NMR spectrum of pleuromulin 7-chloro-1-cyclopropyl-6-fluoro-1,4-dihydro-4-oxoquinoline-3-carboxylic acid ester.
Figure 5:
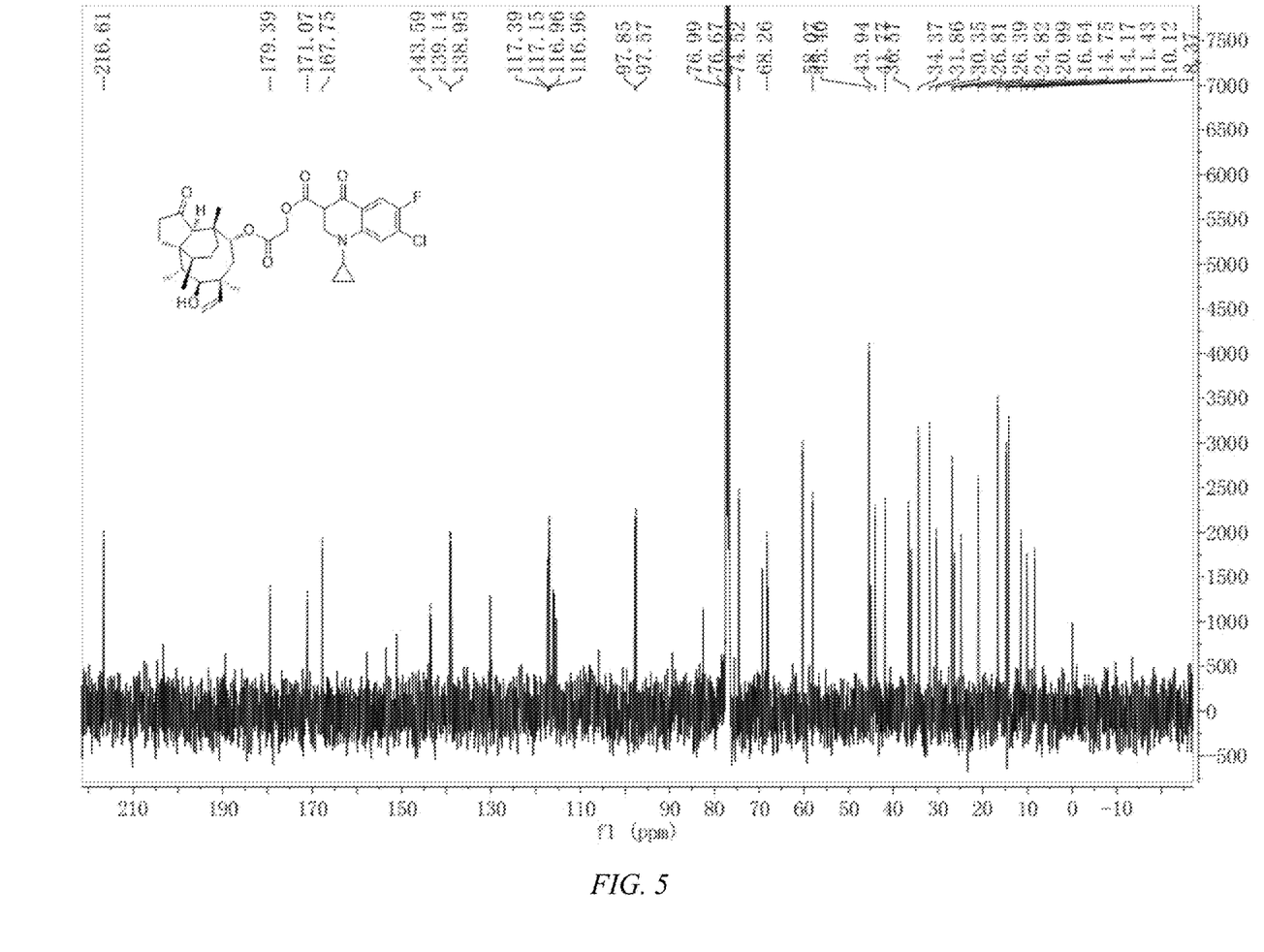
FIG. 5 is the $^{13}$C-NMR spectrum of pleuromulin 7-chloro-1-cyclopropyl-6-fluoro-1,4-dihydro-4-oxoquinoline-3-carboxylic acid ester.

$^1$H-NMR (400 MHz, chloroform-d) δ (ppm): 7.77; (1H, d), 6.55; (1H, m), 5.85; (1H, t), 5.38; (1H, d), 5.28; (2H, s), 5.23; (1H, d), 4.26; (1H, m), 4.19; (1H, m), 4.15; (2H, d), 3.40; (1H, s), 2.95; (1H, m), 2.27-2.14; (4H, m), 2.10; (1H, s), 1.83-1.38; (12H, m), 1.31; (3H, d), 1.22; (3H, d), 0.98; (3H, d), 0.75; (2H, d), 0.67; (2H, d). The $^1$H-NMR spectrum is shown in FIG. 4. $^{13}$C-NMR (400 MHz, Chloroform-d) δ ppm): 216.6, 179.4, 171.1, 167.8, 143.6, 139.1, 139.0, 117.4, 117.2, 117.0, 97.9, 97.6, 74.5, 68.3, 58.1, 45.4, 44.0, 43.9, 41.8, 36.6, 36.0, 34.4, 30.4, 26.8, 26.4, 24.8, 24.0, 16.6, 14.2, 10.1, 8.4. The $^{13}$C-NMR spectrum is shown in FIG. 5.

EXAMPLE 2

Preparation of Compound 2-(((3aS,4R,5S,6S,8R,9R,
9aR,12R)-5-hydroxy-4,6,9,12-tetramethyl-1-oxo-6-
vinyldecahydro-3a,9-propanocyclopenta[8]annulen-
8-yl)oxy)-2-oxoethyl 7-chloro-1-cyclopropyl-6-
fluoro-4-oxo-1,2,3,4-tetrahydroquinoline-3-
carboxylate In a 100 mL three-necked flask, 246.0 mg (0.65 mmol) of pleuromulin and 6.1 mg (0.06 mmol) triethylamine were dissolved in 20 mL of N,N-dimethylformamide, under nitrogen atmosphere. 213.7 mg (0.71 mmol) of 7-chloro-1-cyclopropyl-6-fluoro-1,4-dihydro-4-oxo-quinoline-3-carboxylic acid chloride was dissolved in 20 mL of N,N-dimethylformamide, and added dropwise to the reaction mixture by a separatory funnel. After the completion of the dropwise addition, the reaction was carried out at 25° C. for 4 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:1 as eluent, and the eluent was concentrated under reduced pressure and dried to obtain 265.7 mg of the title compound, a yield of 63.54%.

EXAMPLE 3

Preparation of Compound 2-(((3aS,4R,5S,6S,8R,9R,
9aR,12R)-5-hydroxy-4,6,9,12-tetramethyl-1-oxo-6-
vinyldecahydro-3a,9-propanocyclopenta[8]annulen-
8-yl)oxy)-2-oxoethyl 7-chloro-1-cyclopropyl-6-
fluoro-4-oxo-1,2,3,4-tetrahydroquinoline-3-
carboxylate In a 100 mL three-necked flask, 246.0 mg (0.65 mmol) of pleuromulin and 6.1 mg (0.06 mmol) triethylamine were dissolved in 20 mL of toluene, under nitrogen atmosphere. 213.7 mg (0.71 mmol) of 7-chloro-1-cyclopropyl-6-fluoro-1,4-dihydro-4-oxo-quinoline-3-carboxylic acid chloride was dissolved in 20 mL of toluene, and added dropwise to the reaction mixture by a separatory funnel. After the completion of the dropwise addition, the reaction was carried out at 30° C. for 6 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 269.5 mg of the title compound, a yield of 64.45%.

EXAMPLE 4

Preparation of Compound 2-(((3aS,4R,5S,6S,8R,9R,
9aR,12R)-5-hydroxy-4,6,9,12-tetramethyl-1-oxo-6-
vinyldecahydro-3a,9-propanocyclopenta[8]annulen-
8-yl)oxy)-2-oxoethyl 7-chloro-1-cyclopropyl-6-
fluoro-4-oxo-1,2,3,4-tetrahydroquinoline-3-
carboxylate In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 234.8 mg (0.78 mmol) of 7-chloro-1-cyclopropyl-6-fluoro-1,4-dihydro-4-oxo-quinoline-3-carboxylic acid chloride was dissolved in 20 mL of dichloromethane, and added dropwise to the reaction mixture by a separatory funnel. After the completion of the dropwise addition, the reaction was carried out at 20° C. for 6 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 279.5 mg of the title compound, a yield of 66.85%.

acid ester. The derivative was 279.5 mg, and the total yield was 66.85%.

EXAMPLE 5

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 100 mL three-necked flask, 246.0 mg (0.65 mmol) of pleuromulin and 6.1 mg (0.06 mmol) triethylamine were dissolved in 20 mL of N,N-dimethylformamide, under nitrogen atmosphere. 234.8 mg (0.78 mmol) of 7-chloro-1-cyclopropyl-6-fluoro-1,4-dihydro-4-oxo-quinoline-3-carboxylic acid chloride was dissolved in 20 mL of N,N-dimethylformamide, and added dropwise to the reaction mixture by a separatory funnel. After the completion of the dropwise addition, the reaction was carried out at 40° C. for 4 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 270.0 mg of the title compound, a yield of 64.57%.

EXAMPLE 6

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 255.9 mg (0.85 mmol) of 7-chloro-1-cyclopropyl-6-fluoro-1,4-dihydro-4-oxo-quinoline-3-carboxylic acid chloride was dissolved in 20 mL of dichloromethane, and added dropwise to the reaction mixture by a separatory funnel. After the completion of the dropwise addition, the reaction was carried out at 40° C. for 5 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 283.1 mg of the title compound, a yield of 67.71%.

EXAMPLE 7

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 100 mL three-necked flask, 246.0 mg (0.65 mmol) of pleuromulin and 6.1 mg (0.06 mmol) triethylamine were dissolved in 20 mL of toluene, under nitrogen atmosphere. 216.7 mg (0.72 mmol) of 7-chloro-1-cyclopropyl-6-fluoro-1,4-dihydro-4-oxo-quinoline-3-carboxylic acid chloride was dissolved in 20 mL of toluene, and added dropwise to the reaction mixture by a separatory funnel. After the completion of the dropwise addition, the reaction was carried out at 60° C. for 3 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 261.5 mg of the title compound, a yield of 62.53%.

EXAMPLE 8

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 234.9 mg (0.78 mmol) of 7-chloro-1-cyclopropyl-6-fluoro-1,4-dihydro-4-oxo-quinoline-3-carboxylic acid chloride was dissolved in 20 mL of dichloromethane, and added dropwise to the reaction mixture by a separatory funnel. After the completion of the dropwise addition, the reaction was carried out at 50° C. for 5 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 281.6 mg of the title compound, a yield of 67.35%.

EXAMPLE 9

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 100 mL three-necked flask, 246.0 mg (0.65 mmol) of pleuromulin and 6.1 mg (0.06 mmol) triethylamine were dissolved in 20 mL of toluene, under nitrogen atmosphere. 234.8 mg (0.78 mmol) of 7-chloro-1-cyclopropyl-6-fluoro-1,4-dihydro-4-oxo-quinoline-3-carboxylic acid chloride was dissolved in 20 mL of toluene, and added dropwise to the reaction mixture by a separatory funnel. After the completion of the dropwise addition, the reaction was carried out at 50° C. for 5 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:1 as eluent, and the eluent was concentrated under reduced pressure and dried to obtain 268.4 mg of the title compound, a yield of 64.18%.

EXAMPLE 10

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 100 mL three-necked flask, 246.0 mg (0.65 mmol) of pleuromulin and 6.1 mg (0.06 mmol) triethylamine were dissolved in 20 mL of toluene, under nitrogen atmosphere. 195.7 mg (0.65 mmol) of 7-chloro-1-cyclopropyl-6-fluoro-1,4-dihydro-4-oxo-quinoline-3-carboxylic acid chloride was dissolved in 20 mL of toluene, and added dropwise to the reaction mixture by a separatory funnel. After the completion of the dropwise addition, the reaction was carried out at 20° C. for 6 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 265.3 mg of the title compound, a yield of 63.45%.

EXAMPLE 11

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 216.7 mg (0.72 mmol) of 7-chloro-1-cyclopropyl-6-fluoro-1,4-dihydro-4-oxo-quinoline-3-carboxylic acid chloride was dissolved in 20 mL of dichloromethane, and added dropwise to the reaction mixture by a separatory funnel. After the completion of the dropwise addition, the reaction was carried out at 35° C. for 4 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 274.9 mg of the title compound, a yield of 65.74%.

EXAMPLE 12

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 195.7 mg (0.65 mmol) of 7-chloro-1-cyclopropyl-6-fluoro-1,4-dihydro-4-oxo-quinoline-3-carboxylic acid chloride was dissolved in 20 mL of dichloromethane, and added dropwise to the reaction mixture by a separatory funnel. After the completion of the dropwise addition, the reaction was carried out at 30° C. for 6 hours. Thin layer chromatography was used to track the reaction to completion, heating was stopped, and then the protective device was removed. The reaction mixture was washed with water, extracted with ethyl acetate, concentrated and dried to obtain a crude product. The crude product was purified by silica gel column chromatography, with petroleum ether/ethyl acetate=3:2 as eluent, and the eluent was concentrated under reduced pressure and dried to obtain 282.4 mg of the title compound, a yield of 67.3%.

EXAMPLE 13

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 250 mL three-necked flask, 246.0 mg (0.65 mmol) of pleuromulin, 202.8 mg (0.72 mmol) of 7-chloro-1-cyclopropyl-6-fluoro-1,4-dihydro-4-oxoquinoline-3-carboxylic acid and 12.0 mg (0.007 mmol) silicomolybdic acid were dissolved in 100 mL of 1-butyl-3-methylimidazolium tetrafluoroborate under nitrogen atmosphere. After full dissolution, the temperature of the reaction mixture was raised to 30° C. and the reaction was carried out for 6 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered for reuse. The crude product was recrystallized with 30 mL methanol to obtain 361.8 mg of the title compound, a yield of 86.54%.

EXAMPLE 14

Preparation of Compound 2-(((3aS,4R,5S,6S,8R,9R, 9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 250 mL three-necked flask, 246.0 mg (0.65 mmol) of pleuromulin, 202.8 mg (0.72 mmol) of 7-chloro-1-cyclopropyl-6-fluoro-1,4-dihydro-4-oxoquinoline-3-carboxylic acid and 12.0 mg (0.007 mmol) silicomolybdic acid were dissolved in 100 mL of 1-butyl-3-methylimidazolium tetrafluoroborate under nitrogen atmosphere. After full dissolution, the temperature of the reaction mixture was raised to 20° C. and the reaction was carried out for 8 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered for reuse. The crude product was recrystallized with 30 mL methanol to obtain 332.2 mg of the title compound, a yield of 79.46%.

EXAMPLE 15

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 250 mL three-necked flask, 246.0 mg (0.65 mmol) of pleuromulin, 202.8 mg (0.72 mmol) of 7-chloro-1-cyclopropyl-6-fluoro-1,4-dihydro-4-oxoquinoline-3-carboxylic acid and 12.0 mg (0.007 mmol) silicomolybdic acid were dissolved in 100 mL of 1-octyl-3-methylimidazolium hexafluorophosphate under nitrogen atmosphere. After full dissolution, the temperature of the reaction mixture was raised to 40° C. and the reaction was carried out for 6 hours. Thin layer chromatography was used to track the reaction to completion, heating was stopped, and the protective device was removed. The reaction mixture system was allowed to separate into layers to give a crude product. 1-Octyl-3-methylimidazolium hexafluoro-phosphate was recovered for reuse. The crude product was recrystallized with 30 mL methanol to obtain 324.1 mg of the title compound, a yield of 77.52%.

EXAMPLE 16

Preparation of Compound 2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl 7-chloro-1-cyclopropyl-6-fluoro-4-oxo-1,2,3,4-tetrahydroquinoline-3-carboxylate In a 250 mL three-necked flask, 246.0 mg (0.65 mmol) of pleuromulin, 202.8 mg (0.72 mmol) of 7-chloro-1-cyclopropyl-6-fluoro-1,4-dihydro-4-oxoquinoline-3-carboxylic acid and 12.0 mg (0.007 mmol) silicomolybdic acid were dissolved in 100 mL of 1-hexyl-3-methylimidazolium tetrafluoroborate under nitrogen atmosphere. After full dissolution, the temperature of the reaction mixture was raised to 30° C. and the reaction was carried out for 5 hours. Thin layer chromatography was used to track the reaction to completion, heating was stopped, and the protective device was removed. The reaction mixture system was allowed to separate into layers to give a crude product. 1-Hexyl-3-methylimidazolium tetrafluoroborate was recovered for reuse. The crude product was recrystallized with 30 mL methanol to obtain 310.7 mg of the title compound, a yield of 74.31%.

EXAMPLE 17

Antibacterial Activity Test of the Compounds of the Invention

The antimicrobial efficacy was determined by a paper diffusion method drug sensitivity test.

Experimental strains: multi-resistant *Staphylococcus aureus* 206 (MRSA-206), multi-resistant *Staphylococcus aureus* 575 (MRSA-575), multi-resistant *Staphylococcus aureus* 596 (MRSA-596). The experimental strain was identified by Huashan Hospital Affiliated to Fudan University (Institute of Antibiotic of Fudan University).

Drug sensitive paper: The drug sensitive paper was a special drug sensitive paper with a diameter of 6.35 mm and a water absorption of 0.02 mL. The control drug was vancomycin (30 μg/tablet); the test drugs were pleuromulin (30 μg/tablet), 7-chloro-1-cyclopropyl-6-fluoro-1,4-dihydro-4-oxoquinoline-3-carboxylic acid (30 μg/tablet) and pleuromulin 7-chloro-1-cyclopropyl-6-fluoro-1,4-dihydro-4-oxoquinoline-3-carboxylic acid ester (30 μg/tablet).

Reagents: LB agar medium, LA broth medium, 0.5% DMSO solution.

Equipment: Ultra-clean workbench, high-pressure sterilization pot, gas bath constant temperature shaking incubator.

Preparation of Bacterial Suspension

The experimental strains were inoculated in non-selective medium and placed in air at 37° C. for 24 h. A single colony that grows well and inoculate it into broth medium was incubate at 35° C.±2° C. for 6 hours, and LA broth medium was used to calibrate the concentration of the bacterial solution to 0.5 Mie turbidimetric tube ($1.5 \times 10^8$ CFU/mL). A bacterial suspension was obtained.

Paper Diffusion Method Drug Sensitivity Test

LB dry powder was weighed, sterilized at 103.4 Kpa, 121.3° C. high-pressure steam for 15 min, and then placed it in a 40° C.-50° C. water bath. A sterile empty plate (inner diameter 9 cm) was placed on the surface of the ultra-clean table water table, and LB dry powder was poured to the plate. The thickness of each plate was 3 mm to 4 mm. After the plate was cooled at room temperature, it was stored in the refrigerator at 2° C.-8° C. A sterile cotton swab was used to dip the bacterial solution and to evenly coat the surface of the LB plate 3 times. After inoculation of the bacterial suspension, the LB plate was dried at room temperature for 3 min to 5 min. Sterile forceps were used to closely attach the antibacterial drug paper to the dish. The dish was put upside down and placed in a 37° C. incubator for 24 h. The results were observed by measuring the diameter. Taking 0.5% DMSO solution as a negative control, the antibacterial activity is expressed by the diameter of the inhibition zone. The inhibition zone>17 mm, sensitive; the inhibition zone of 15 mm-16 mm, intermediary; the inhibition zone<14 mm, drug resistance.

Figure 1:
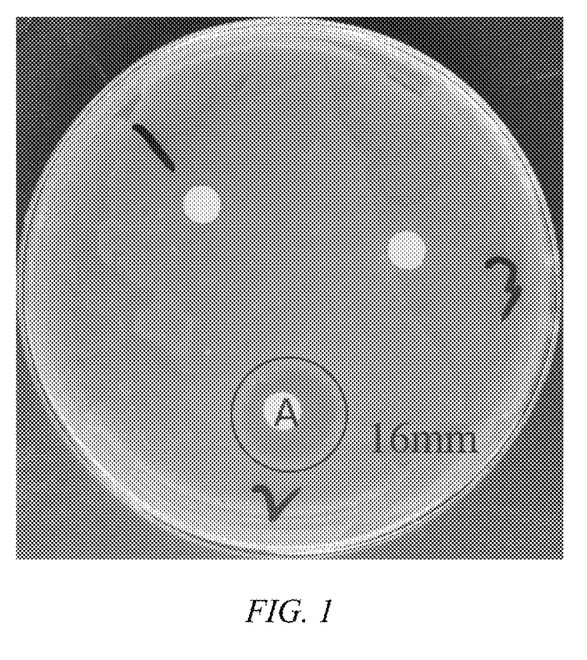
FIG. 1 shows the in vitro antibacterial activity of pleuromulin 7-chloro-1-cyclopropyl-6-fluoro-1,4-dihydro-4-oxoquinoline-3-carboxylic acid ester against drug-resistant bacteria MARS 18-206.
Figure 2:
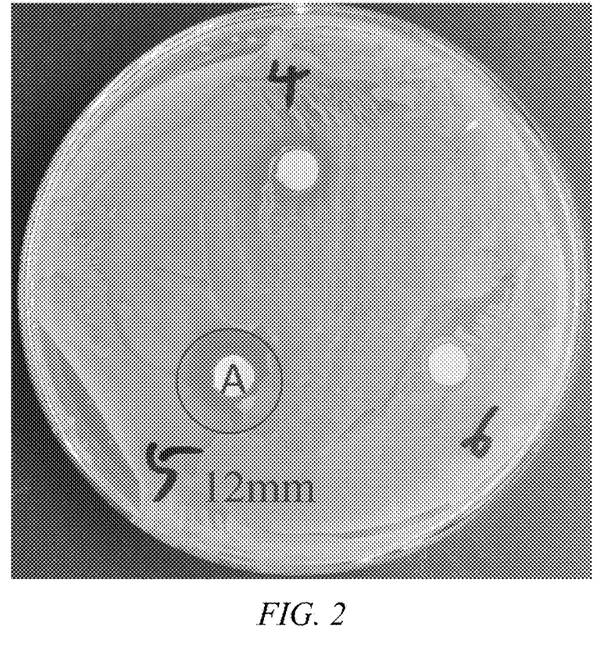
FIG. 2 shows the in vitro antibacterial activity of pleuromulin 7-chloro-1-cyclopropyl-6-fluoro-1,4-dihydro-4-oxoquinoline-3-carboxylic acid ester against drug-resistant bacteria MARS 18-575.
Figure 3:
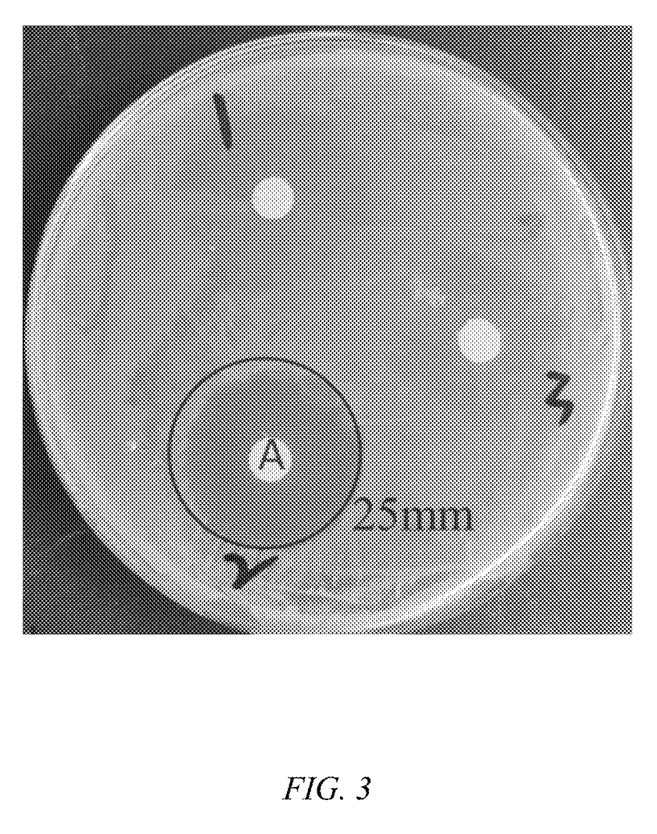
FIG. 3 shows the in vitro antibacterial activity of pleuromulin 7-chloro-1-cyclopropyl-6-fluoro-1,4-dihydro-4-oxoquinoline-3-carboxylic acid ester against drug-resistant bacteria MARS 18-596.

In FIGS. 1-3, pleuromulin 7-chloro-1-cyclopropyl-6-fluoro-1,4-dihydro-4-oxoquinoline-3-carboxylic acid ester is represented by the letter A. FIG. 1 shows the antibacterial effect of pleuromulin 7-chloro-1-cyclopropyl-6-fluoro-1,4-dihydro-4-oxoquino-line-3-carboxylic acid ester on MRSA-206. FIG. 2 shows the antibacterial effect of pleuromulin 7-chloro-1-cyclopropyl-6-fluoro-1,4-dihydro-4-oxoquino-line-3-carboxylic acid ester on MRSA-575. FIG. 3 shows the antibacterial effect of pleuromulin 7-chloro-1-cyclopropyl-6-fluoro-1,4-dihydro-4-oxoquinoline-3-carboxylic acid ester on MRSA-596. The results are shown in Table 1.

TABLE 1

Experimental results of the zone of inhibition

| Compound | Zone of inhibition/mm Strain | | |
|---|---|---|---|
| | MRSA-206 | MRSA-575 | MRSA-596 |
| 0.5% DMSO | 0 | 0 | 0 |
| Vancomycin | 15 | 17 | 23 |
| Pleuromulin | 0 | 0 | 0 |
| 7-Chloro-1-cyclopropyl-6-fluoro-1,4-dihydro-4-oxoquinoline-3-carboxylic acid | 0 | 0 | 0 |
| Pleuromulin 7-chloro-1-cyclopropyl-6-fluoro-1,4-dihydro-4-oxo-quinoline-3-carboxylic acid ester | 16 | 12 | 25 |

The results in FIGS. 1-3 and Table 1 show that the starting materials pleuromutilin and 7-chloro-1-cyclopropyl-6-fluoro-1,4-dihydro-4-oxoquinoline-3-carboxylic acid have no inhibitory effect on drug-resistant bacteria. Pleuromulin 7-chloro-1-cyclopropyl-6-fluoro-1,4-dihydro-4-oxoquinoline-3-carboxylic acid ester has strong inhibitory effects on multi-drug resistant *Staphylococcus aureus* 206, 575, 596, and the diameter of bacteriostatic zone against multidrug resistant *Staphylococcus aureus* 596 was up to 25 mm. In summary, pleuromulin 7-chloro-1-cyclopropyl-6-fluoro-1,4-dihydro-4-oxoquinoline-3-carboxylic acid ester of the present invention can be used as an antibacterial drug candidate for multi-drug resistant *Staphylococcus aureus*.

What is claimed is:

1. A compound having the following formula (I):

(I)

2. A method of preparing the compound of formula (I) of claim 1, comprising:
reacting a compound of formula (II) with a compound of formula (III) to obtain the compound of formula (I):

(II)

+

(III)

→

(I)

3. The method of claim 2, wherein the compound of formula (III) is prepared by the following steps:
adding 7-chloro-1-cyclopropyl-6-fluoro-1,4-dihydro-4-oxoquinoline-3-carboxylic acid to dichloromethane as a reaction solvent in a reactor;
adding oxalyl chloride and N,N-dimethylformamide as a catalyst to the reactor under nitrogen atmosphere;
stirring at 20° C. for 3 hours; and
removing the reaction solvent to obtain the compound of formula (III).

4. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalytic amount of triethylamine under nitrogen atmosphere to obtain a reaction mixture; and
heating the reaction mixture at 20-60° C. for 3-6 hours; and
extracting the reaction mixture with ethyl acetate to obtain a crude product; and
purifying the crude product on a silica gel fresh chromatography column with dichloromethane and ethyl acetate as an eluent to obtain the compound of formula (I).

5. The method of claim 4, wherein the organic solvent is toluene, dichloromethane or N,N-dimethylformamide.

6. The method of claim 5, wherein the organic solvent is dichloromethane.

7. The method of claim 4, wherein the molar ratio of the compound of formula (II) and the compound of formula (III) is 1:1.1.

8. The method of claim 4, wherein the reaction mixture is heated at 25° C.

9. The method of claim 4, wherein the reaction mixture is heated for 5 hours.

10. A method of preparing the compound of formula (I) of claim 1, comprising:
reacting the compound of formula (II) with the compound of formula (IV) to obtain the compound of formula (I):

11. The method of claim 10, wherein the reaction of the compound of formula (II) with the compound of formula (IV) comprises the following steps:

placing the compound of formula (II), a catalyst, and an ionic liquid in a reactor under nitrogen atmosphere, the catalyst being 12-molybdosilicic acid hydrate ($H_6Mo_{12}O_{41}Si$);

adding the compound of formula (IV) to the reactor to form a reaction mixture;

heating the reaction mixture at 20-50° C. for 4-8 hours;

placing the reaction mixture in a separating funnel to separate a crude product;

purifying the crude product by recrystallization in methanol to obtain the compound of formula (I); and recycling the ionic liquid.

12. The method of claim 11, wherein the ionic liquid is 1-octyl-3-methylimidazo-lium hexafluorophosphate, 1-hexyl-3-methylimidazolium tetrafluoroborate, or 1-butyl-3-methylimidazolium tetrafluoroborate ([BMIM][BF$_4$]).

13. The method of claim 11, wherein the compound of formula (II) and the compound (IV) have a molar ratio of 1:1 to 1:1.3.

14. The method of claim 13, wherein the molar ratio of the compound of formula (II) and the compound of formula (IV) is 1:1.1.

15. The method of claim 11, wherein the reaction mixture is heated at 30° C.

16. The method of claim 11, wherein the reaction mixture is heated for 6 hours.

* * * * *